(12) United States Patent
Borer et al.

(10) Patent No.: US 10,845,280 B2
(45) Date of Patent: Nov. 24, 2020

(54) INTEGRATED WEDGE FOR TESTING FABRIC ON SIDE ACTING PNEUMATIC GRIPS

(71) Applicants: ILLINOIS TOOL WORKS INC., Glenview, IL (US); Kevin Robert Borer, Quincy, MA (US); Ray Hewenson Tong, Foxborough, MA (US)

(72) Inventors: Kevin Robert Borer, Quincy, MA (US); Ray Hewenson Tong, Foxborough, MA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 83 days.

(21) Appl. No.: 16/089,487

(22) PCT Filed: Mar. 7, 2017

(86) PCT No.: PCT/US2017/021063
§ 371 (c)(1),
(2) Date: Sep. 28, 2018

(87) PCT Pub. No.: WO2017/172292
PCT Pub. Date: Oct. 5, 2017

(65) Prior Publication Data
US 2019/0107473 A1    Apr. 11, 2019

Related U.S. Application Data

(60) Provisional application No. 62/316,805, filed on Apr. 1, 2016.

(51) Int. Cl.
*G01N 3/04* (2006.01)
*G01N 33/36* (2006.01)

(52) U.S. Cl.
CPC .............. *G01N 3/04* (2013.01); *G01N 33/367* (2013.01); *G01N 2203/0017* (2013.01); *G01N 2203/0252* (2013.01); *G01N 2203/0282* (2013.01)

(58) Field of Classification Search
CPC .................. G01N 3/04; G01N 33/367; G01N 2203/0017; G01N 2203/0252; G01N 2203/0282
(Continued)

(56) References Cited

U.S. PATENT DOCUMENTS 2,327,139 A * 8/1943 Scott ................... G01N 3/04
                                                       73/858
5,224,386 A * 7/1993 Curtis ................... G01N 3/04
                                                       73/833
(Continued)

FOREIGN PATENT DOCUMENTS

SU        1232989    *   5/1986

OTHER PUBLICATIONS

International Search Report issued in PCT/US2017/021063 dated May 29, 2017.
(Continued)

*Primary Examiner* — Octavia Hollington
(74) *Attorney, Agent, or Firm* — McCarter & English LLP (57) ABSTRACT

The present disclosure relates to a device to be used with materials testing of fabrics, wherein the materials testing apparatus includes grips with opposing jaw faces. A wedge is provided which is mounted on a bracket which is attached to the grip. The wedge is used to increase surface area of the material against the jaw faces of the grips, which increases the ability of the grips to hold onto the sample/specimen/material during test. The wedge can slide in the bracket or
(Continued)

the wedge mount can slide in the bracket to allow it to self-center itself in the grip body.

17 Claims, 9 Drawing Sheets

(58) Field of Classification Search
USPC .......................................................... 73/856
See application file for complete search history.

(56) References Cited

U.S. PATENT DOCUMENTS

| | | | | |
|---|---|---|---|---|
| 5,297,441 | A * | 3/1994 | Smith | ..................... G01N 3/04 |
| | | | | 73/818 |
| 6,176,142 | B1 | 1/2001 | Ericson | |
| 6,860,156 | B1 | 3/2005 | Cavallaro et al. | |
| 8,448,522 | B2 * | 5/2013 | Martin | ..................... G01N 3/04 |
| | | | | 73/856 |
| 8,459,623 | B2 * | 6/2013 | Tsai | ..................... B25J 15/0266 |
| | | | | 269/134 |
| 8,757,004 | B2 * | 6/2014 | Martin | ..................... G01N 3/04 |
| | | | | 73/856 |
| 9,021,889 | B2 * | 5/2015 | Gaddum | ................... G01N 3/02 |
| | | | | 73/856 |
| 2014/0331782 | A1 * | 11/2014 | Keranen | ................... H05B 3/32 |
| | | | | 73/856 |

OTHER PUBLICATIONS

XP-002770089 SU 1 232 989 A; Cotton Ind. Res. Inst., Database WPI Clarivate Analytics, Thomson Scientific, London, GB, 1987-013690; May 23, 1986 Abstract.

* cited by examiner

INTEGRATED WEDGE FOR TESTING FABRIC ON SIDE ACTING PNEUMATIC GRIPS

FIELD OF THE DISCLOSURE

The present disclosure relates to a device to be used with materials testing of fabrics or similar materials, wherein the materials testing apparatus includes grips with opposing jaw faces to exert a tensile force on the fabric sample.

BACKGROUND OF THE DISCLOSURE

This application is National Phase application of PCT International Application PCT/US2017/021063, filed on Mar. 7, 2017, which claims priority under 35 U.S.C. 119(e) of U.S. provisional application Ser. No. 62/316,805 filed on Apr. 1, 2016, the contents of which is hereby incorporated by reference in its entirety and for all purposes.

DESCRIPTION OF THE PRIOR ART

In the prior art of materials testing of fabrics using grips with opposing jaw faces, it is known to wrap fabrics around a drum of a capstan grip to prevent jaw breaks or jaw slippage. Similarly, it is known to wrap cord or yarn around a smooth curved surface of a cord or yarn grip.

However, prior art grip design may be incapable of gripping some materials to required loads, which may result in specimen slippage and failed tests. Moreover, prior art devices may require two or more distinct sets of grips for different materials, one set for typical specimens such as metal or plastic, and a second set (cord or yarn grips or capstan grips) to allow for testing of fabric.

Additionally, in the prior art, alignment may be based on the mounting and assembly quality of the fabric grips. Misalignment frequently cannot be accounted for without permanent modification to the grips.

SUMMARY OF THE DISCLOSURE

The disclosure relates to a device for materials testing, including a bracket and a wedge, around which a strip of fabric or similar sample material can be wrapped. After installation in the grip, the wedge and the material are held between the jaw faces of the grip. The wedge is used to increase the surface area of the material against the jaw faces, which increases the grips' ability to securely hold the sample/specimen/material during the test. The wedge can slide in the bracket thereby allowing it to self-center itself in the grip body. The self-centering allows the upper and lower jaws of the grip to be offset to allow an "S" wrap of a fabric, which may be required for some testing protocols.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENT

Figure 1:
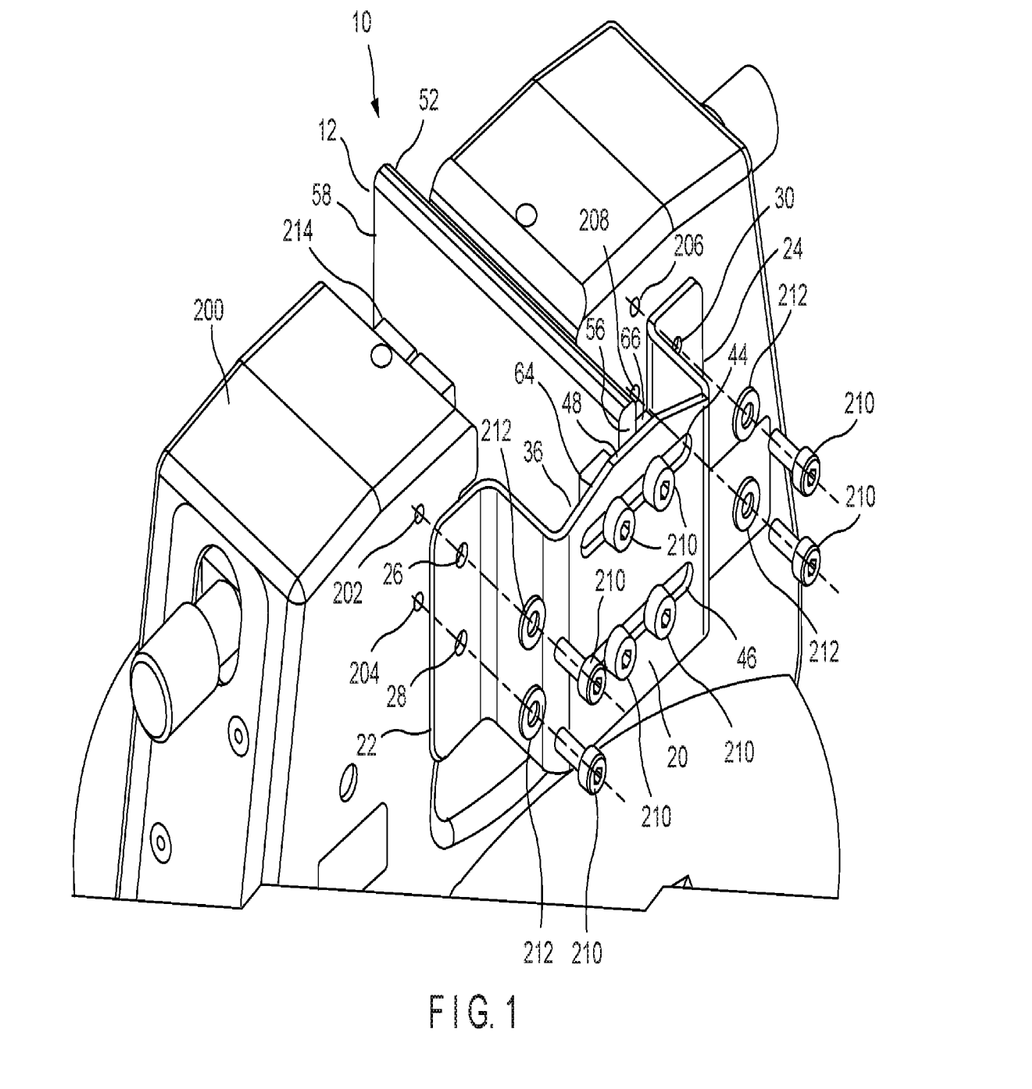
FIG. 1 is a perspective view of the wedge assembly, including a wedge and a wedge mount, installed on the grip of materials testing device, in an embodiment of the present disclosure.
Figure 3A:
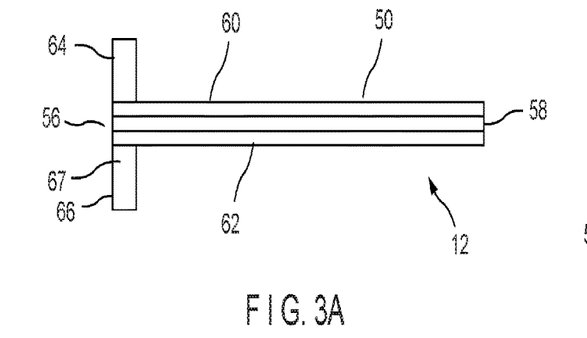
FIG. 3A is a top plan view of wedge in an embodiment of the wedge assembly of the present disclosure.
Figure 3B:
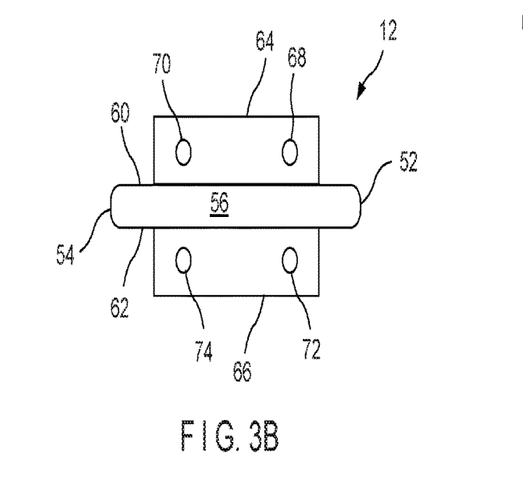
FIG. 3B is a side plan view of the wedge in an embodiment of the wedge assembly of the present disclosure.
Figure 3C:
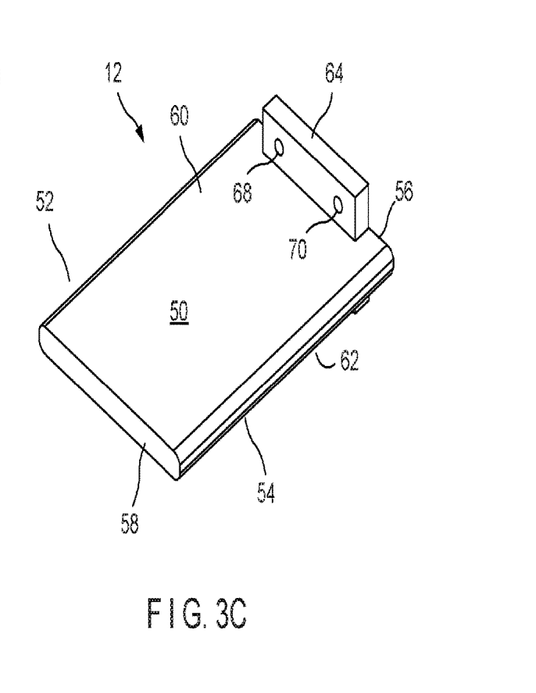
FIG. 3C is a perspective view of the wedge in an embodiment of the wedge assembly of the present disclosure.
Figure 4:
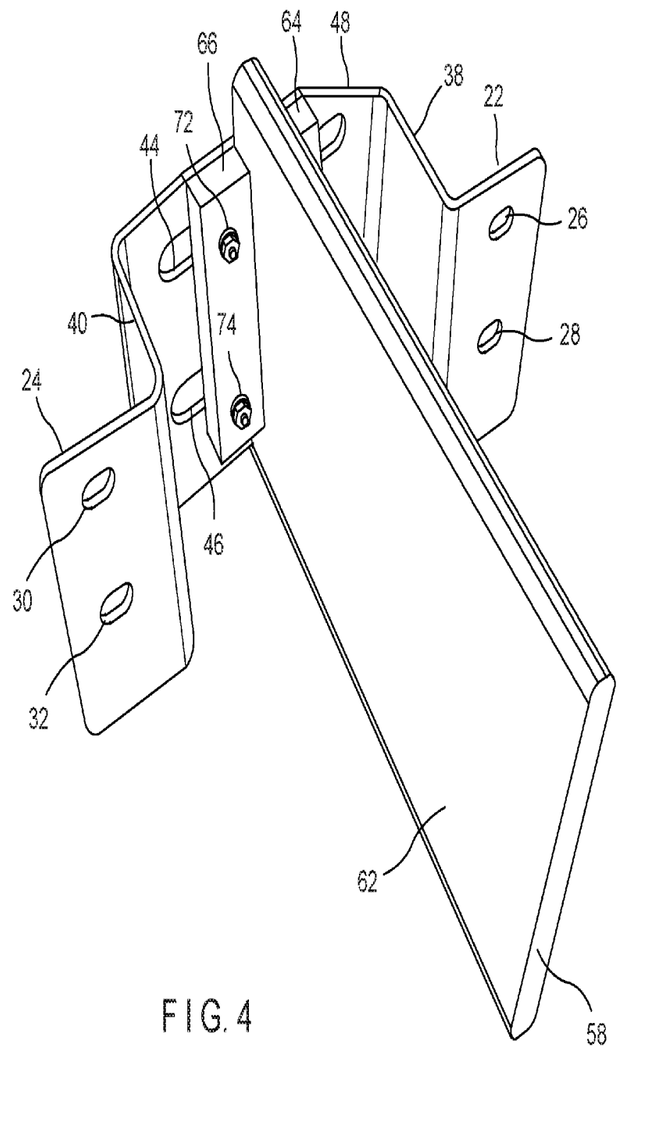
FIGS. 4 and 5 are perspective views of the wedge attached to the wedge mount, in an embodiment of the wedge assembly of the present disclosure.
Figure 5:
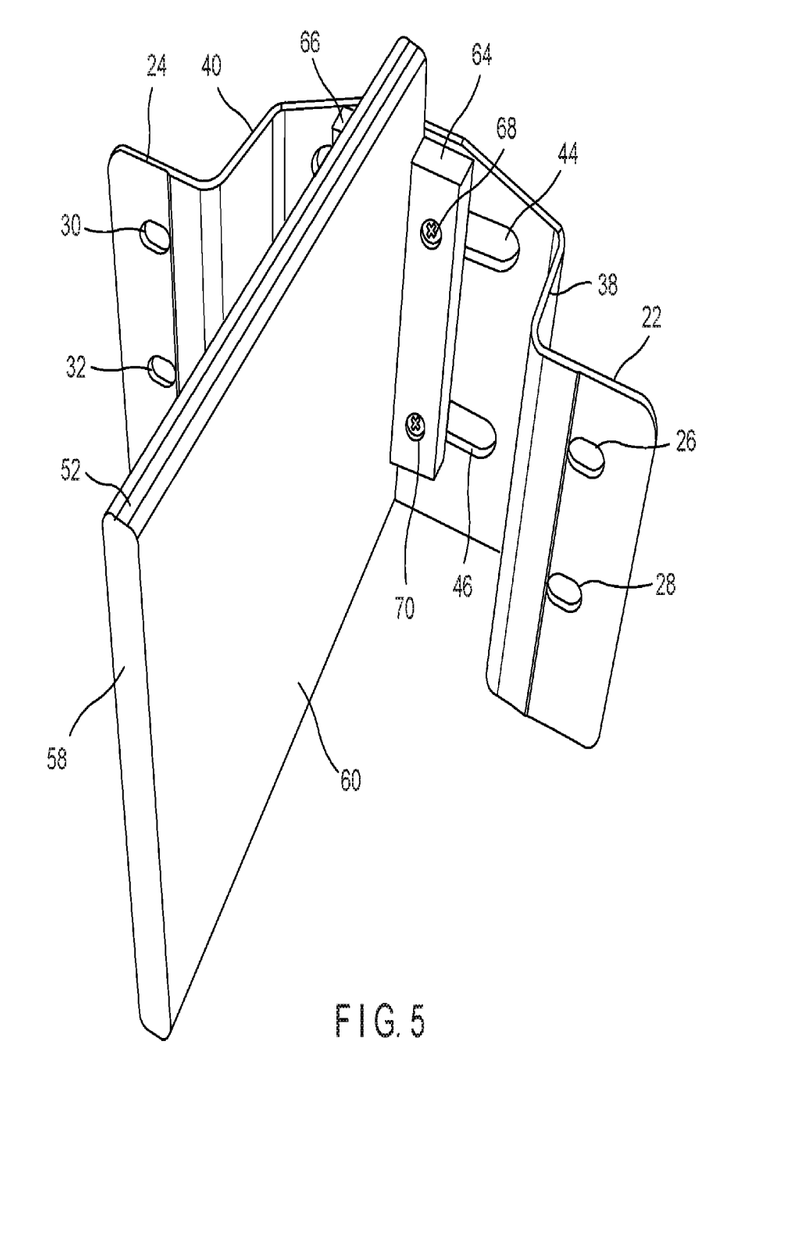
Figure 6:
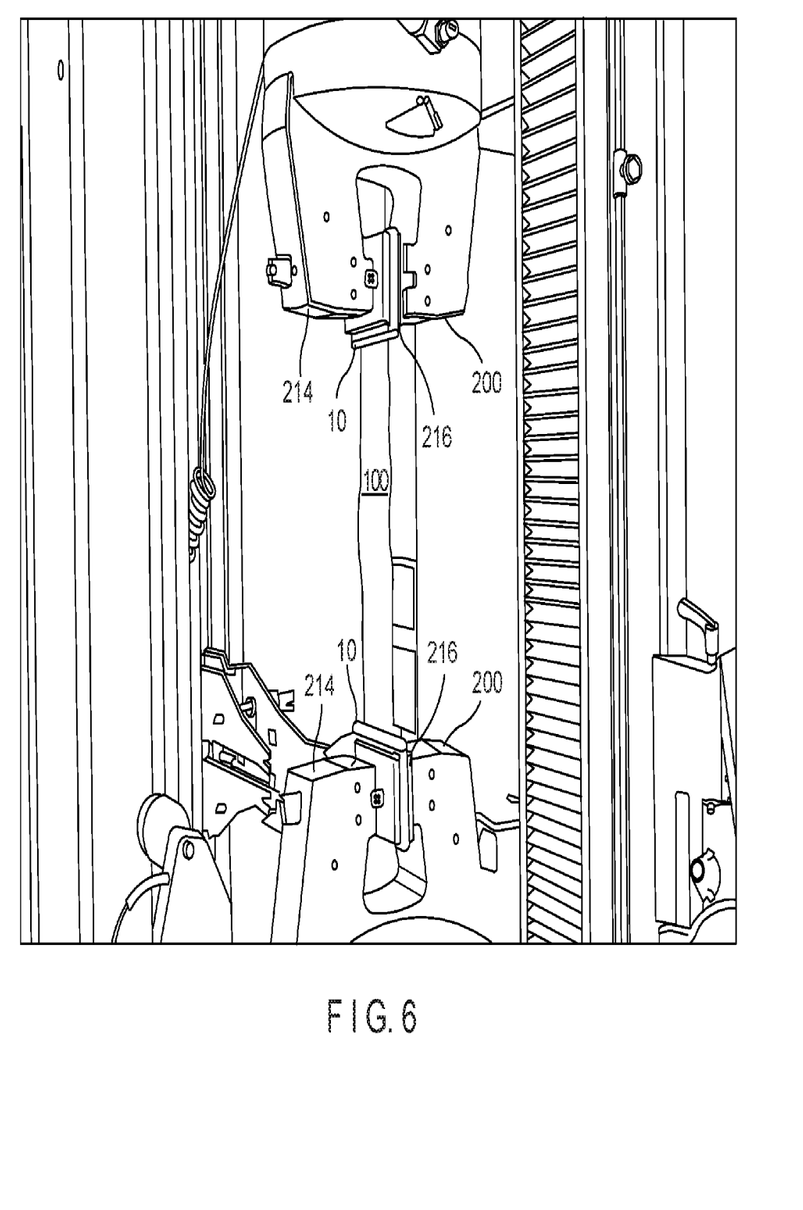
FIGS. 6-9 are perspective views of an embodiment of the present disclosure, in a materials testing environment.
Figure 7:
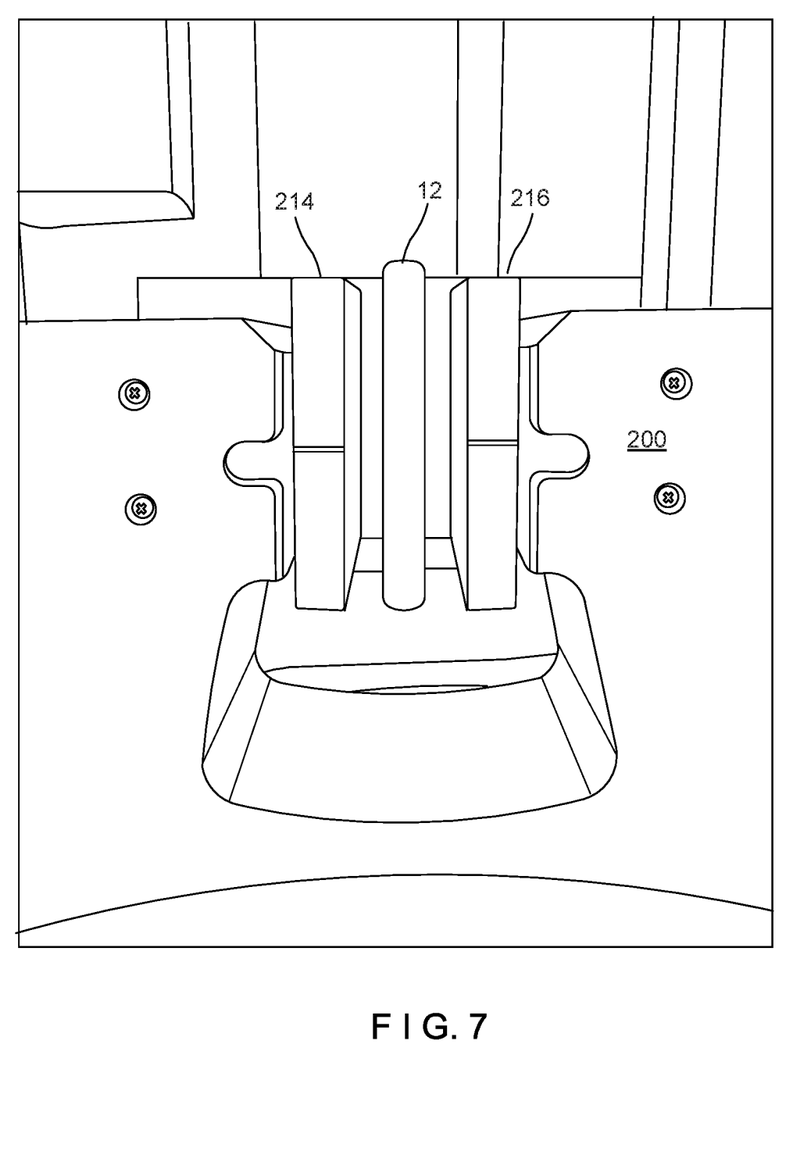
Figure 8:
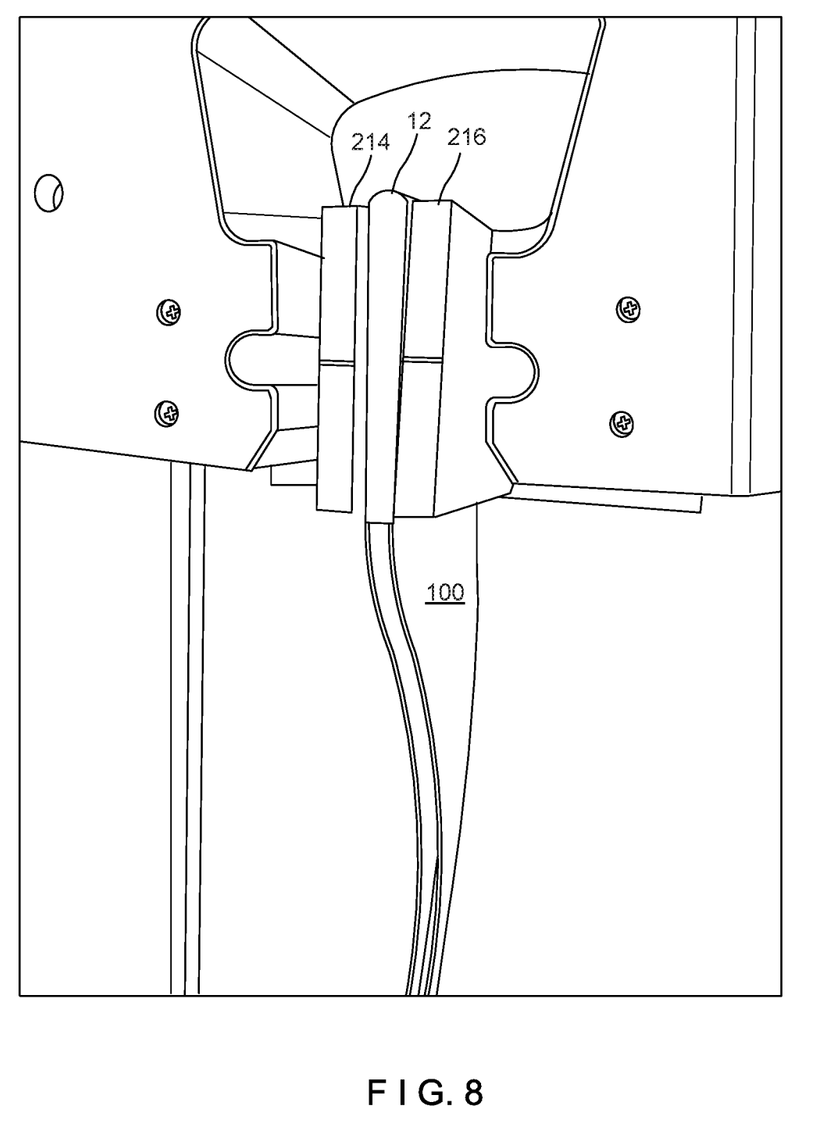
Figure 9:
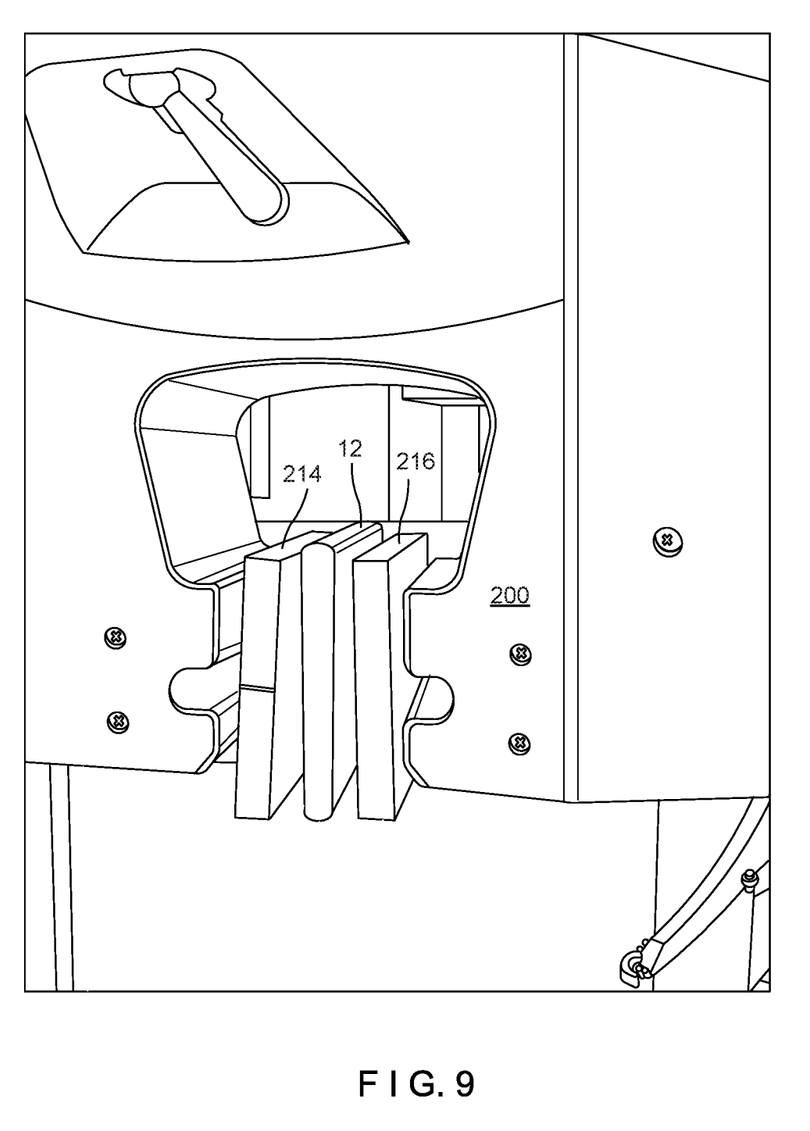

Referring now to the drawings in detail wherein like numerals refer to like elements throughout the several views, one sees that FIG. 1 illustrates the wedge assembly 10, which includes wedge 12 (also see FIGS. 3A-3C) mounted on the bracket or wedge mount 20 (also see FIGS. 2A-2C) which is, in turn, secured to the grip 200 (typically a side-acting pneumatic grip) by bolts (or screws) 210 and washers 212 (also see FIGS. 4 and 5). As shown in FIG. 6, the grips 200, each with a wedge assembly 10, including a wedge 12 and wedge mount 20, are typically supplied in a vertically opposed pair in a materials testing apparatus to provide a tensile (i.e., pulling apart) load on a fabric material sample 10.

Figure 2A:
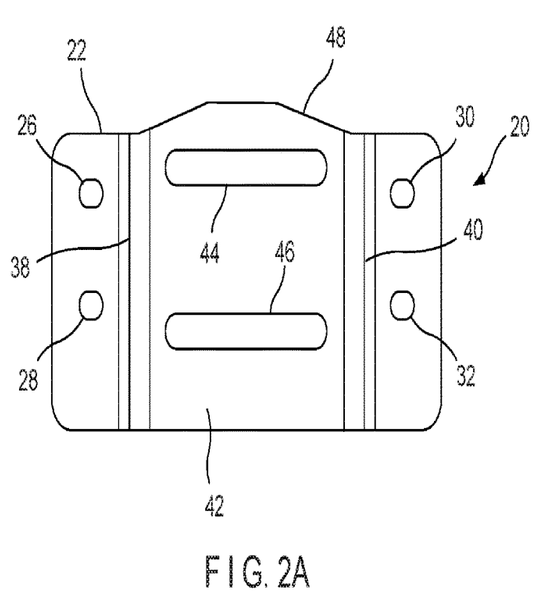
FIG. 2A is a front plan view of the wedge mount in an embodiment of the wedge assembly of the present disclosure.
Figure 2B:
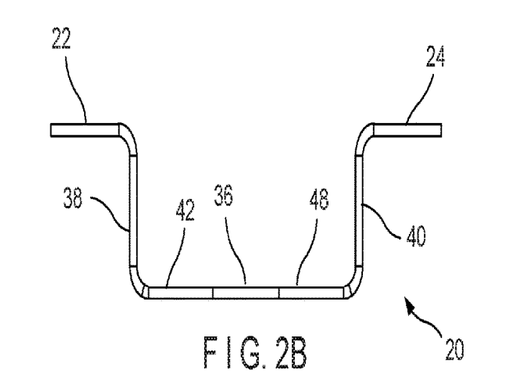
FIG. 2B is a top plan view of the wedge mount in an embodiment of the wedge assembly of the present disclosure.
Figure 2C:
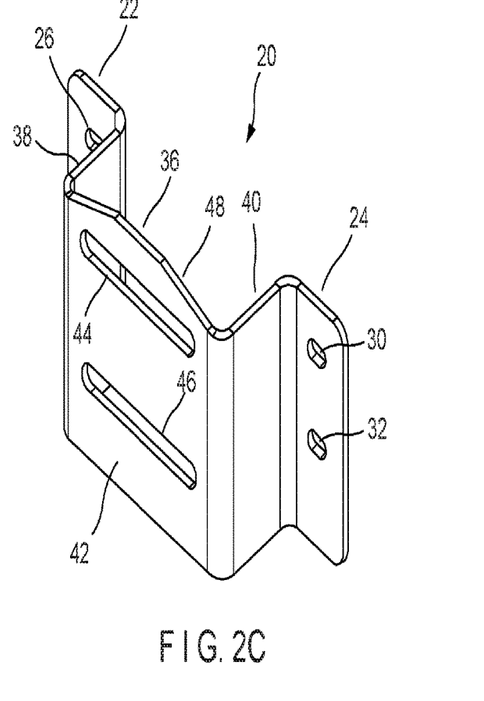
FIG. 2C is a perspective view of the wedge mount in an embodiment of the wedge assembly of the present disclosure.

As shown in more detail in FIGS. 2A, 2B and 2C, the wedge mount 20 is typically made from a single piece of stainless steel or similar material and includes first and second lateral flanges 22, 24, which are co-planar, so as to mounted on the stationery grip 200 as shown in FIG. 1. The first lateral flange 22 includes mounting apertures 26, 28 which are vertically aligned with each other and which, as shown in FIG. 1, receive bolts (or screws) 210 (typically with washers 212 mounted concentrically thereon) which are, in turn, threadably secured to the threaded apertures 202, 204 of the grip 200. Likewise, the second lateral flange 24 includes mounting apertures 30, 32 which are vertically aligned with each other and which, as shown in FIG. 1, receive bolts (or screws) 210 (typically with washers 212 mounted concentrically thereon) which are, in turn, threadably secured to the threaded apertures 206, 208 of the grip 100. As illustrated, mounting apertures 26, 28, 30, 32 may be oval-shaped with a horizontal major axis to allow the ability to horizontally adjust the final position of the wedge mount 20 with respect to the grip 200 before final tightening of the bolts 210, and additionally to allow for flexure of the grips 200 when the grips 200 are applying horizontal side-acting forces via jaw faces 214, 216 while bolts 210 are not fully tightened.

The wedge mount 20 further includes an offset U-shaped portion 36, typically made from stainless steel or a similar material, between the first and second lateral flanges 22, 24. The offset U-shaped portion 36 includes first and second sidewalls 38, 40 which are generally perpendicular to (with rounded transition areas) the respective first and second lateral flanges 22, 24 and further includes central offset mounting plate 42 which extends between first and second sidewalls 38, 40. Central offset mounting plate 42 is typically perpendicular to (with rounded transition areas) first and second sidewalls 38, 40 and is parallel to, and offset from, first and lateral flanges 22, 24. The central offset mounting plate 42 includes upper and lower horizontal mounting slots 44, 46 which are parallel to each other. The upper edge of central mounting plate 42 may have an upwardly extending sloped portion 48 in order to provide structural reinforcement, particularly with respect to upper horizontal mounting slot 44.

As shown in FIGS. 3A, 3B and 3C, the wedge 12 includes a rectangular planar body 50, typically with top and bottom rounded edges 52, 54 to accommodate the wrapping of the fabric sample 100 thereabout (see FIGS. 6-9) and squared-off front and rear edges 56, 58. The planar body 50 therefore includes first and second planar engagement surfaces 60, 62. First and second mounting flanges 64, 66 extend from respective first and second planar engagement surfaces 60, 62 adjacent to front edge 56 thereby presenting a mounting surface 67 co-planar with front edge 56, and perpendicular to first and second planar engagement surfaces 60, 62. First mounting flange 64 presents first and second threaded mounting apertures 68, 70 oriented horizontally with respect to each other (in the orientation illustrated in FIG. 1). Similarly, second mounting flange 66 presents third and fourth threaded mounting apertures 72, 74 oriented horizontally with respect to each other (in the orientation illustrated in FIG. 1).

In order to mount the wedge 12 on wedge mount 10, as shown in FIG. 1 (as well as FIGS. 4 and 5 and in order to reach the operational configuration of FIGS. 6-9), the mounting surface 67 of wedge 12 is abutted against the interior of offset U-shaped portion 36 of wedge mount 20. Two bolts 210 pass through upper horizontal mounting slot 44 and are threadably received by first and third threaded mounting apertures 68, 72. Likewise, two bolts 210 pass through lower horizontal mounting slot 46 and are threadably received by second and fourth threaded mounting apertures 70, 74. The relative position of the wedge 12 to the wedge mount 20 can be adjusted or varied by adjusting or varying the position of bolts 210 within upper and lower mounting slots 44, 46. The bolts 210 through upper and lower horizontal mounting slots 44, 46 may be less than fully tightened, thereby allowing for self-centering of the wedge 12 under the extreme pressure of the jaw faces 214, 216 of the grip 200. In some applications, the bolts 210 may be sufficiently tightened to prevent or minimize subsequent movement of the wedge 12 with respect to the wedge mount 20. In particular, it is typically important to have the wedge 12 properly positioned so that equal pressure is applied to first and second planar engagement surfaces 60, 62 (with fabric material sample 100 wrapped around wedge 12) by the first and second opposed (movable) jaw faces 214, 216 of the grip 200.

Before commencing testing, the wedge mount 20 is mounted on the grip 200 and the position of the wedge 12 is adjusted so as to be properly positioned for wrapping a fabric material sample 100 therearound. Once installed in the grip 200, the wedge 12 and material 100 are held between the jaw faces of the grip 200 (see FIG. 1). The wedge 12 is used to increase surface area of the material 100 against the jaw faces 214, 216 of the grips 200, which increases the ability of the grips 200 to hold onto the sample/specimen/material during test. The wedge 12 can slide in the bracket or wedge mount 20 can slide in the bracket to allow it to self-center itself in the grip 200 in response to the forces applied by the jaw faces 214, 216 of the grips 200. Wedge mount 20 can further accommodate flexure of grips 200 when grips 200 are applying horizontal side-acting loads via jaw faces 214, 216 This self-centering allows the upper and lower jaws of the grip 200 to be offset to allow an "S" wrap of a strip of material or fabric sample 100. Moreover, as the wedge 12 translates along the upper and lower horizontal mounting slots, typically the wedge 12 does not rotate and maintains a vertical orientation.

It is envisioned that many embodiments of the present disclosure will have such advantages as: the mounting to existing grips to expand testing capability; the use of a passive device to double the surface area of contact between the jaw faces and the test specimen (fabric sample); the slotted mounting bracket allows self-centering of the test specimen (fabric sample) to prevent or minimize off-centered loading of the device; allowing expanded capability of standard opposing jaw face grips to include testing of fabrics and other materials that are typically problematic for these types of grips; and modular and quick change capabilities, in that it can use different combinations of wedges (which may include various surface finishes) and custom jaw faces that can be quickly changed out.

Thus the several aforementioned objects and advantages are most effectively attained. Although preferred embodiments of the invention have been disclosed and described in detail herein, it should be understood that this invention is in no sense limited thereby.

What is claimed is:

1. An assembly for engaging a sample in a materials testing device, comprising:
   a mounting device for engaging a grip of a materials testing device; and
   a sample receiving device mounted on the mounting device and extending between first and second jaw faces of a grip of a materials testing device, the sample receiving device including a first planar surface and a second planar surface, the first and second planar surfaces oriented toward respective first and second jaw faces of a grip of a materials testing device, thereby gripping a sample contacted by and between the first planar surface of the sample receiving device and a first jaw face of a materials testing device and thereby further gripping a sample contacted by and between the second planar surface of the sample receiving device and a second jaw face of a grip of a materials testing device.

2. The assembly of claim 1 wherein the sample receiving device includes upper and lower rounded edges.

3. The assembly of claim 1 wherein at least one of the first and second planar surfaces includes a mounting flange extending therefrom.

4. The assembly of claim 1 wherein the first and second planar surfaces include respective first and second mounting flanges therefrom.

5. The assembly of claim 4 wherein the first and second mounting flanges present a mounting surface.

6. The assembly of claim 5 wherein the mounting surface is planar and perpendicular to the first and second planar surface.

7. The assembly of claim 5 wherein the mounting device includes first and second grip engaging flanges for attaching to a grip of a materials testing device.

8. The assembly of claim 7 wherein the first and second grip engaging flanges are co-planar with each other.

9. The assembly of claim 8 wherein the first and second grip engaging flanges includes apertures for receiving bolts which are threadably received by a grip of a materials testing device.

10. The assembly of claim 9 wherein the mounting device further includes a U-shaped portion between the first and second grip engaging flanges.

11. The assembly of claim 10 wherein the U-shaped portion includes a mounting plate parallel to and offset from the first and second grip engaging flanges.

12. The assembly of claim 11 wherein the mounting plate includes at least one slot for receiving bolts which are received by the mounting surface of the sample receiving device.

13. The assembly of claim 11 wherein the mounting plate includes first and second slot for receiving bolts which are received by threaded apertures in the mounting surface of the sample receiving device.

14. The assembly of claim 11 wherein the sample receiving device can translate along the first and second slots without rotation.

15. The assembly of claim 13 wherein the sample receiving device has a rectangular shape.

16. The assembly of claim 11 wherein the mounting device and the sample receiving device are made from stainless steel.

17. The assembly of claim 1 wherein a sample is wrapped around an exterior of the sample receiving device.

* * * * *